United States Patent
Jin et al.

(10) Patent No.: US 10,711,005 B2
(45) Date of Patent: Jul. 14, 2020

(54) COMPOUND I AND COMPOUND II AS WELL AS PREPARATION METHODS THEREFOR AND APPLICATION THEREOF

(71) Applicants: SHENZHEN UNIVERSITY, Shenzhen, Guangdong (CN); SHENZHEN KANGJUZHENG PHARMACEUTICAL TECHNOLOGY CO., LTD., Shenzhen, Guangdong (CN)

(72) Inventors: Guangyi Jin, Guangdong (CN); Zhulin Wang, Guangdong (CN)

(73) Assignees: SHENZHEN UNIVERSITY, Shenzhen (CN); SHENZHEN KANGJUZHENG PHARMACEUTICAL TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/776,784

(22) PCT Filed: Nov. 8, 2016

(86) PCT No.: PCT/CN2016/105101
§ 371 (c)(1),
(2) Date: May 16, 2018

(87) PCT Pub. No.: WO2017/084519
PCT Pub. Date: May 26, 2017

(65) Prior Publication Data
US 2018/0339987 A1 Nov. 29, 2018

(30) Foreign Application Priority Data
Nov. 16, 2015 (CN) .......................... 2015 1 0786141

(51) Int. Cl.
C07D 487/04 (2006.01)
C07D 473/18 (2006.01)
A61K 31/519 (2006.01)
C07K 1/107 (2006.01)
C07K 14/705 (2006.01)

(52) U.S. Cl.
CPC .......... *C07D 487/04* (2013.01); *A61K 31/519* (2013.01); *C07D 473/18* (2013.01); *C07K 1/107* (2013.01); *C07K 14/70503* (2013.01)

(58) Field of Classification Search
CPC .... C07D 473/18; C07K 1/107; C07K 14/705; A61P 35/00; A61K 31/519
USPC ....................................... 544/265; 514/263.3
See application file for complete search history.

(56) References Cited

U.S. PATENT DOCUMENTS
2018/0339987 A1* 11/2018 Jin ....................... C07D 473/18

FOREIGN PATENT DOCUMENTS
CN 102993265 A 3/2013
TW 201124134 A1 7/2011

OTHER PUBLICATIONS

Zhu, Jiang et al., Local Administration of a Novel Toll-Like Receptor 7 Agonist in Combination with Doxorubicin Induces Durable Tumouricidal Effects in a Murine Model of T Cell Lymphoma, Journal of Hematology & Oncology, Mar. 4, 2015, pp. 1-10, vol. 8, No. 21.

* cited by examiner

*Primary Examiner* — Venkataraman Balasubramanian

(57) ABSTRACT

Compound I and a compound II as well as preparation methods therefor and use thereof are disclosed. A newly synthesized compound of formula I is capable of stimulating congenital immunity and cellular immunity for tumor resistance while greatly improving the antitumor effect of ethacrynic acid (EA), and thus an integrated synergistic anti-tumor dual-immunity drug design is explored. The immune response mechanism for resisting melanoma of the compound as shown in the formula I is demonstrated. A compound that is as shown in a formula II and is prepared from the compound of formula I and ROR1 by means of covalency markedly slows down the growth of subcutaneously transplanted mammary cancer tumor, such that the immune response mechanism, for treating the mammary cancer, of the compound as shown in the formula II is demonstrated.

9 Claims, 9 Drawing Sheets

Specification includes a Sequence Listing.

SEQUENCE LISTING

<160> NUMBER OF SEQ ID NOS: 7

<210> SEQ ID NO 1
<211> LENGTH: 27
<212> TYPE: PRT
<213> ORGANISM: Artificial Sequence
<220> FEATURE:
<223> OTHER INFORMATION: Synthetic

<400> SEQUENCE: 1

Gly Thr Leu Ser Ser His Pro Pro Val Pro Thr Cys Ala Gly Thr Ser
1               5                   10                  15

Ser Val Ser Pro Gly Val Val Leu Thr Gly Ile
            20                  25

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Pro Tyr Cys Asp Glu Thr Ser Ser Val 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Glu Tyr Leu Ser Ser His Phe Phe Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Ser Phe Gly Val Val Leu Trp Glu Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Leu Tyr Leu Pro Gly Met Asp His Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Asp Phe Leu His Ile Ala Ile Gln Ile
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Tyr Tyr Gly Phe Ser Asn Gln Glu Val
1               5

COMPOUND I AND COMPOUND II AS WELL AS PREPARATION METHODS THEREFOR AND APPLICATION THEREOF

REFERENCE TO SEQUENCE LISTING

The substitute Sequence Listing is submitted to replace the previously submitted sequence listing as an ASCII formatted text file via EFS-Web, with a file name of "Substitute Sequence Listing.txt", a creation date of Jun. 5, 2020, and a size of 1,880 bytes. The Sequence Listing filed via EFS-Web is part of the specification and is incorporated in its entirety by reference herein.

TECHNICAL FIELD

The present disclosure relates generally to a technical filed of tumor and cancer prevention and treatment, and more particularly, to a compound I and a compound II as well as preparation methods therefor and use thereof.

BACKGROUND

Malignant melanoma which belongs to a highly malignant tumor derived from melanocytes, is a common malignant tumor in skin cancer and has a strong metastasis. The main treatment method is radiotherapy, chemotherapy and surgical treatment, however, such traditional treatments cannot completely cure it. With the development of immunology and molecular biology, the tumor immunotherapy has become a hot topic of research. Toll like receptor (TLRs), an important class of pattern recognition receptors, belongs to type I transmembrane proteins, and is expressed in various immune cells. TLRs play an important role in stimulating the process of innate and adaptive immune responses. The agonists of TLRs act on antigen presenting cells, such as dendritic Cell (DC), to promote the production of cytokines and thus better stimulate the immune response. TLR7 (Toll like receptor 7) is one of the Toll like receptors whose ligand is mainly a nucleic acid component of the virus, and it can also identify some synthetic small molecular agonists. A stronger immune response can be triggered when TLR7 is activated. T7 (the first reagent) is an agonist of a small chemical molecule TLR7 receptor synthesized by the Shenzhen synthetic biology engineering laboratory of Shenzhen University. It is reported that T7 has the ability to improve innate immunity. When it is reacted with dendritic cells derived from bone marrow cells in vitro, inflammatory mediators, such as TNF-a and IL-12 can be produced rapidly, meanwhile when it is reacted with lymphocyte, inflammatory mediators, such as IFN-γ and IL-12 can also be produced rapidly. The source and preparation process of T7 may refers to "Local administration of a novel Toll-like receptor 7 agonist in combination with doxorubicin induces durable tumoricidal effects in a murine model of T cell lymphoma" *Journal of Hematology & Oncology.* 2015, Mar. 4; 8(1):21, doi: 10.1186/s13045-015-0121-9". Ethacrynic acid (EA, the second reagent), also called as diuretic acid, is a diuretic. It has been reported that EA has a variety of anti-tumor effects, but it cannot stimulate the specific anti-tumor cell immune response, which makes its anti-tumor effect poor and its side effects obvious, thus the tumor cells relapse and grow repeatedly.

Mammary cancer is a malignant tumor occurring in the mammary gland epithelial tissue. The majority of the patients are female, and patients of advanced stage are prone to have tumor cells metastases. At present, the main treatments of mammary cancer are surgical treatment, radiotherapy and chemotherapy. However, the radiotherapy and chemotherapy can kill normal cells while killing tumor cells, which would seriously destroy the immune system of the human body. Tumor biotherapy is the fourth way of tumor treatment, in which the tumor immunotherapy is a promising and better treatment for mammary cancer. The purpose of tumor immunotherapy is to stimulate or mobilize the immune system of the human body, enhance the anti-tumor immunity of the tumor microenvironment, and induce the human body to produce immune cells that can effectively identify the tumor related antigen, so as to control and kill the tumor cells. ROR1 (Receptor-tyrosine-kinase-like orphan receptor, the third reagent) is a typical type I receptor-tyrosine-kinase-like orphan receptor surface protein. It is found that ROR1 is expressed in many human-derived tumor cell lines. Moreover, ROR1 is highly expressed in mammary tumor cells, but not expressed in the normal mammary cells, and the expression of ROR1 is related to the growth of the tumor cell. The higher the expression of ROR1, the faster the growth of the tumor. It is reported that the expression of ROR1 is closely related to the early metastasis, recurrence and prognosis of the mammary tumor. The patients with high expression of ROR1 have a short survival time without metastasis than those with low expression. Blocking the expression of ROR1 can significantly inhibit the metastasis of tumor cells to the lung. Therefore, ROR1 can be used to as a target for tumor therapy. However, ROR1 has a weak immunogenicity, so cannot stimulate innate immunity.

SUMMARY

The object of the present application is to provide a compound of formula I and a compound of formula II as well as preparation methods therefor and use thereof, that is a compound I and a compound II as well as preparation methods therefor and use thereof. To be specific, a new compound of formula I is obtained by a coupling of T7 (a first reagent) and EA (a second reagent), and a new compound of formula II is further obtained by a covalent binding of the compound of formula I and ROR1 (a third reagent), aiming at the defects of the poor therapeutic effects and adverse reactions brought by the EA and ROR1 that cannot induce an immune response in the prior art.

In one aspect, there is provided a compound of formula I:

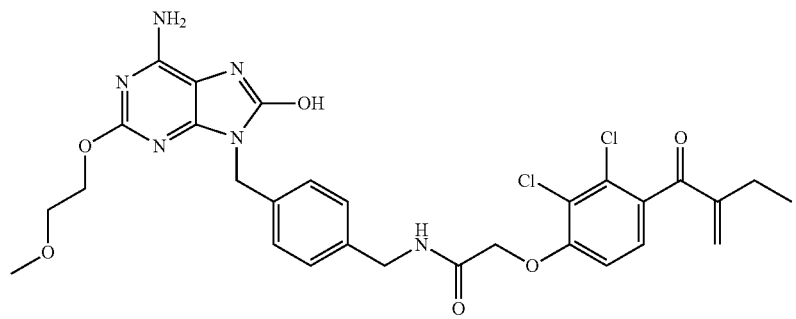

I

In a further aspect, there is provided a preparation method for the compound of formula I, which comprising:

S1, dissolving a first reagent

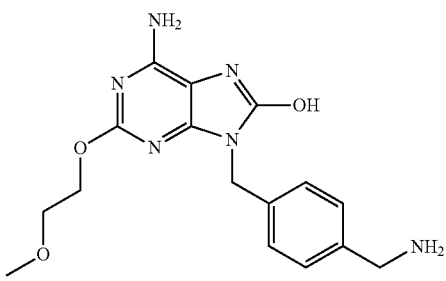 [SMILES: COCCOc1nc(N)c2nc(O)n(Cc3ccc(CN)cc3)c2n1]

and a second reagent EA

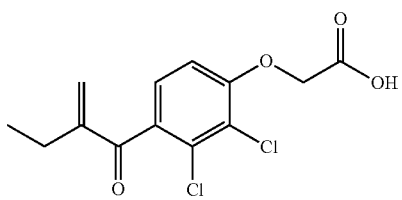 [SMILES: C=C(CC)C(=O)c1ccc(OCC(=O)O)c(Cl)c1Cl]

in a reaction solvent, then adding O-Benzotriazole-N,N,N',N'-tetramethyl-uronium-hexafluorophosphate (HBTU), triethylamine, and 4-Dimethylaminopyridine as a catalyst, and stirring obtained mixture at a room temperature for reaction;

S2, pouring reaction solution obtained after the reaction is completed into water for a suction filtration, then washing and drying residue to obtain the compound of formula I.

In a further embodiment, in the step S1, the first reagent, the second first reagent, the HBTU and the triethylamine are reacted in following parts by mol: the first reagent 4-12 parts, the second first reagent 5-15 parts, the HBTU 5-15 parts and the triethylamine 18-30 parts. Preferably, the first reagent, the second first reagent, the HBTU and the triethylamine are reacted in following parts by mol: the first reagent 6-10 parts, the second first reagent 7-12 parts, the HBTU 7-12 parts and the triethylamine 22-28 parts. More preferably, the first reagent and the second first reagent have a mole ratio of 1:1, While the 4-Dimethylaminopyridine has a catalytic amount.

In a further embodiment, in the step S1, the reaction solvent is selected from one or more of tetrahydrofuran, toluene, benzene, N,N-Dimethylformamide, N,N-dimethylacetamide and N-methylpyrrolidone, wherein N,N-Dimethylformamide is more preferable.

In a further embodiment, the step S1 has a reaction time of 8-24 hours, and preferably 10-15 hours.

In a further embodiment, the preparation method further comprises step S3 which follows step S2: purifying obtained compound of formula I via column chromatography isolation using a mixed solvent of dichloromethane and methanol in a volume ratio of 20:1.

In another aspect, there is provided the use of a compound of formula I for the manufacture of pharmaceuticals for immunological treatment or prevention of skin cancer caused by melanoma.

In another aspect, there is provided a compound of formula II prepared by the compound of formula I:

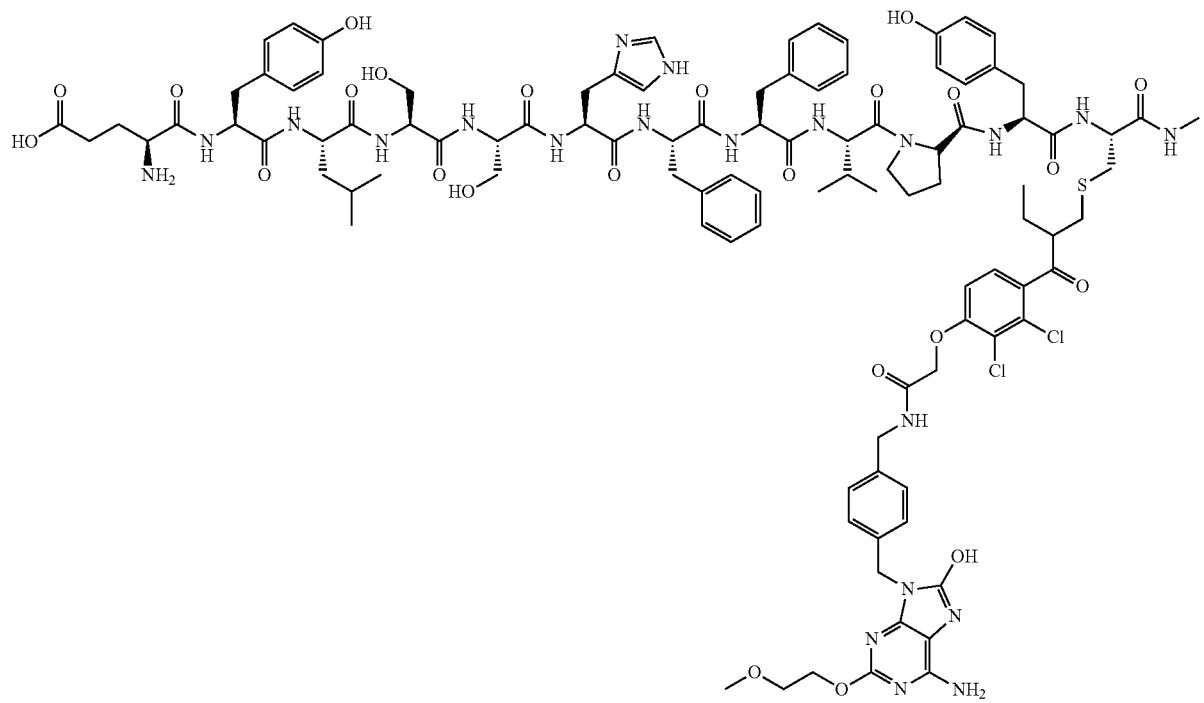

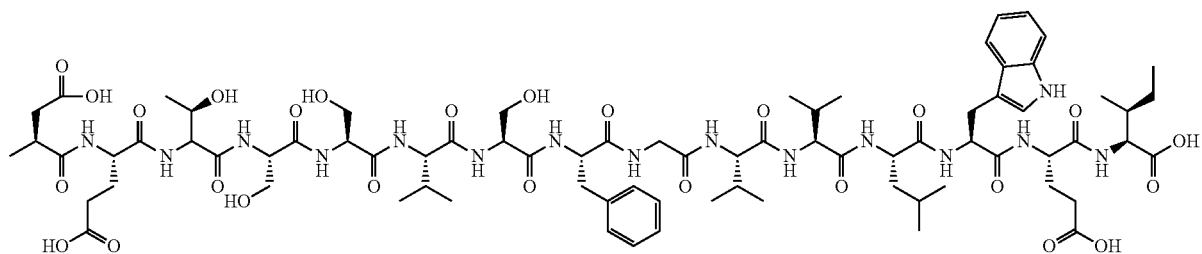

In another aspect, there is provided a preparation method for the compound of formula II, which comprising: dissolving a third reagent into dimethyl sulfoxide and adding the compound of formula I, then stirring for 8-24 hours at room temperature, preferably for 12 hours, and obtaining the compound of formula II by using liquid chromatography-mass spectrometry to monitor reaction and prepare liquid chromatography isolation.

Wherein the third reagent is ROR1 having following formula:

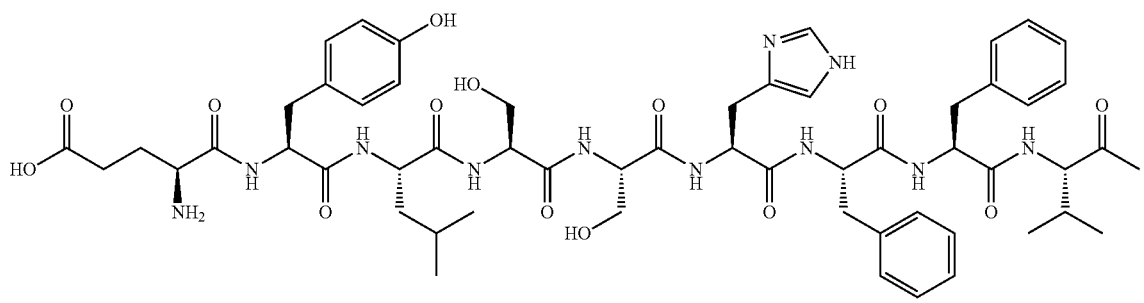

-continued

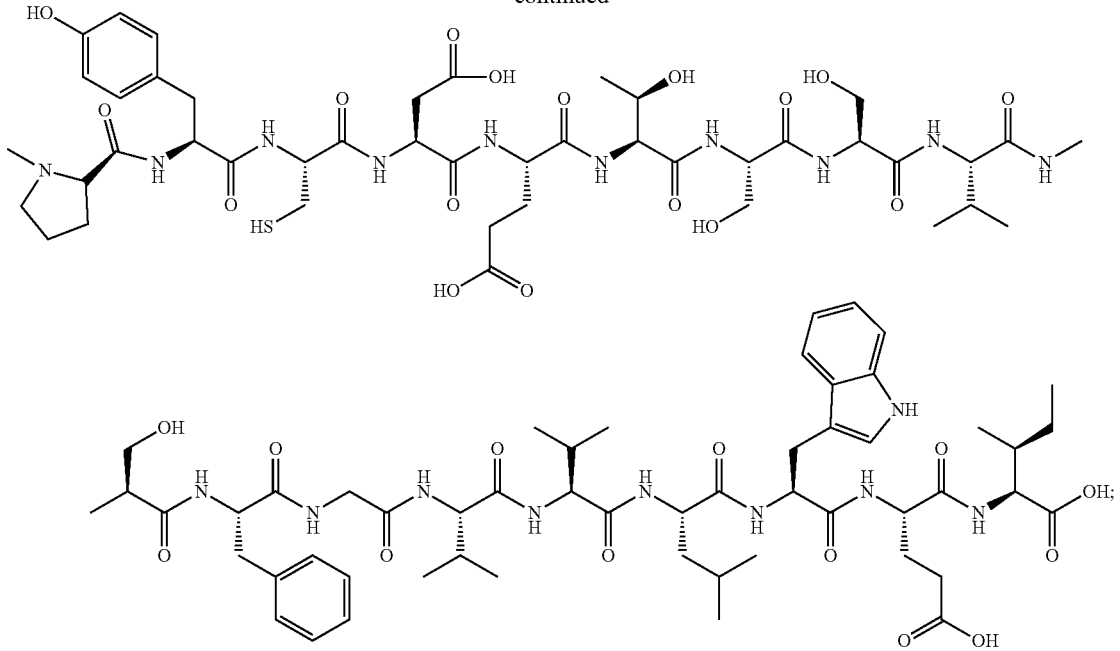

wherein the third reagent and the compound of formula I have a reaction mole ratio of 1:1.

In another aspect, there is provided the use of a compound of formula II for the manufacture of pharmaceuticals for immunological treatment or prevention of mammary cancer.

When implementing the compound of formula I and compound of formula II as well as preparation methods therefor and use thereof, following technical effects will been obtained. The new synthesized compound of formula I in the present application can stimulate the innate and cellular immunity for resisting tumor while greatly improving the antitumor effect of the EA, thus exploring the antitumor and immunity synergistic drug design, and proving the immune response mechanism of the compound of formula I against melanoma. The compound of formula II prepared by the coupling of the compound of formula I and ROR1 has significantly slowed down the growth of the subcutaneous transplantation tumor of the mammary cancer, which proves the immune response mechanism of the compound of formula II against the mammary cancer while proving that the compound of formula II not only just have the function of stimulating the innate and adaptive immunity, but also have an immunologic adjuvant effect.

DETAILED DESCRIPTION OF THE PREFERRED EMBODIMENT

The compound of formula I and compound of formula II as well as preparation methods therefor and use thereof, are further explained by combining the attached drawing and embodiments.

The present application has provided a compound of formula I (short for T7-EA) as follows synthesize by a first reagent (short for T7) and a second reagent (short for EA):

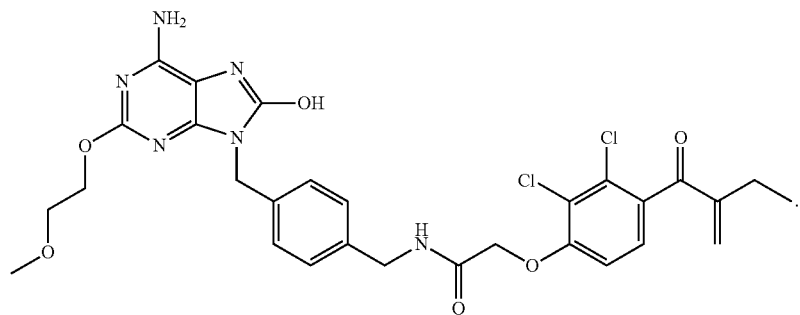 [SMILES: C=C(CC)C(=O)c1ccc(OCC(=O)NCc2ccc(Cn3c(O)nc4c(N)nc(OCCOC)nc43)cc2)c(Cl)c1Cl]

The chemical reaction of the compound of formula I is as follows:

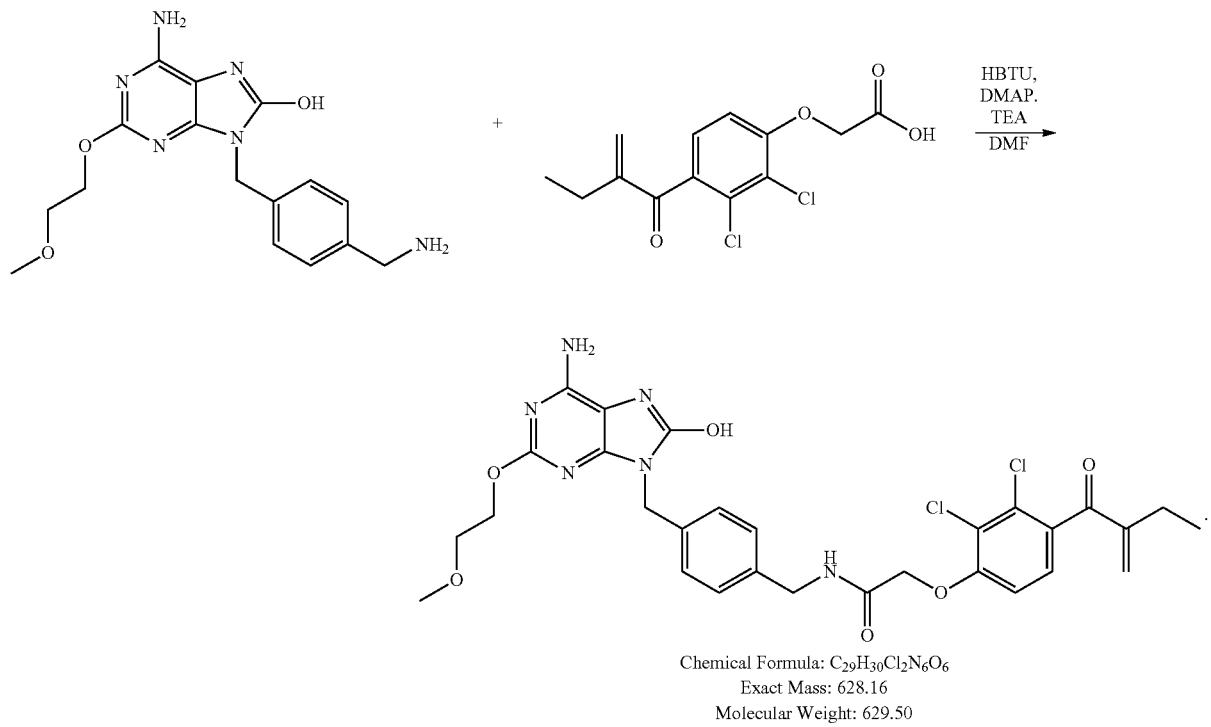

Chemical Formula: $C_{29}H_{30}Cl_2N_6O_6$
Exact Mass: 628.16
Molecular Weight: 629.50

The preparation method for the compound of formula I comprises following steps. The first reagent (short for T7)

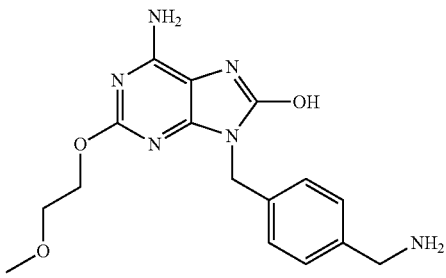 [SMILES: COCCOc1nc(N)c2nc(O)n(Cc3ccc(CN)cc3)c2n1]

and the second reagent (short for EA)

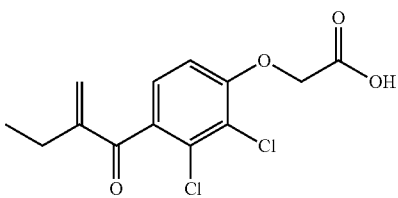 [SMILES: C=C(CC)C(=O)c1ccc(OCC(=O)O)c(Cl)c1Cl]

are dissolved in a reaction solvent. Then the O-Benzotriazole-N,N,N',N'-tetramethyl-uronium-hexafluorophosphate (HBTU), triethylamine (TEA), and 4-Dimethylaminopyridine (DMAP) as a catalyst, are added and then obtained mixture is stirred at a room temperature for reaction. The reaction solution obtained after the reaction is completed is poured into water for a suction filtration. Then the residue is washed and dried to obtain the compound of formula I which is further purified and isolated by column chromatography to obtain white solid compound of formula I. The reaction solvent is selected from one or more of tetrahydrofuran, toluene, benzene, N,N-Dimethylformamide, N,N-dimethylacetamide and N-methylpyrrolidone wherein N,N-Dimethylformamide (DMF) is more preferable.

The source and preparation process of T7 may refers to "Local administration of a novel Toll-like receptor 7 agonist in combination with doxorubicin induces durable tumoricidal effects in a murine model of T cell lymphoma" *Journal of Hematology & Oncology.* 2015, Mar. 4; 8(1):21, doi: 10.1186/s13045-015-0121-9". The second reagent is purchased from Sigma company, USA.

Figure 1:
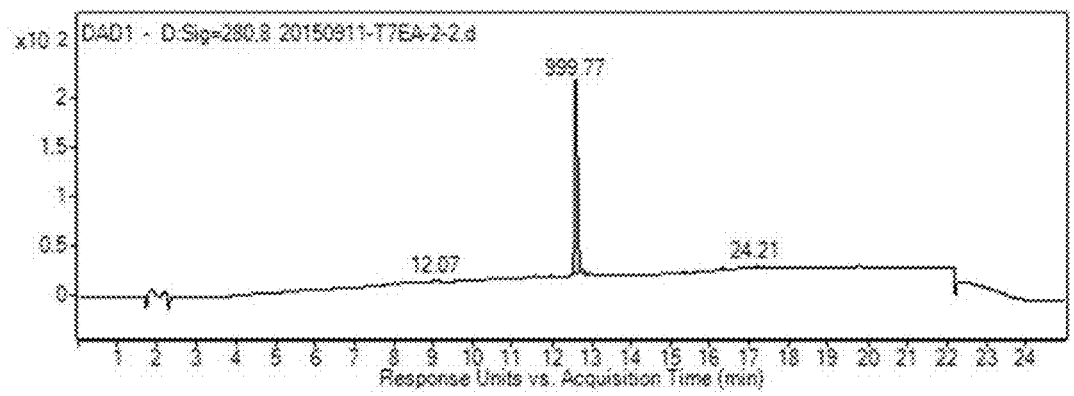
FIG. 1 is a spectrogram of the compound of formula I T7-EA.
Figure 2:
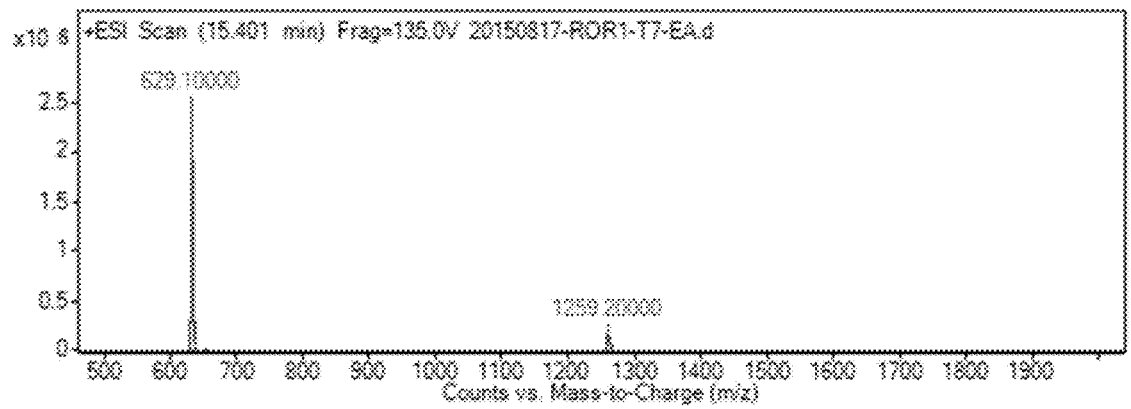
FIG. 2 is a mass spectrogram of the compound of formula I T7-EA.

Embodiment 1 for Preparation of the Compound of Formula I 344 mg (1 mmol) T7 and 341 mg (1.125 mmol) EA are dissolved in 8 mL DMF. HBTU (427 mg, 1.125 mmol), triethylamine (416 µL, 3 mmol) and DMAP of catalytic amount are further added and then obtained mixture is stirred at a room temperature for 12 hours for further reaction. The obtained reaction fluid is poured into 100 mL water for a suction filtration. Then the residue is washed and dried to obtain a crude product. 475 mg white solid T7-EA with a yield of 75.5%, a purity of 95.08%, ESI-MS: m/z=629.1 [M+H]$^+$ (shown in FIGS. 1-2) is obtained after a column chromatography isolation (DCM:MeOH=20:1).

Embodiment 2 for Preparation of the Compound of Formula I 172 mg (0.5 mmol) T7 and 189.4 mg (0.625 mmol) EA are dissolved in 6 mL mixture solvent of benzene and toluene with a volume ratio of 2:1, HBTU (237.2 mg, 0.625 mmol), triethylamine (312 µL, 2.25 mmol) and DMAP of catalytic amount are further added and then obtained mixture is stirred at a room temperature for 24 hours for further reaction. The obtained reaction fluid is poured into 100 mL water for a suction filtration. Then the residue is washed and dried to obtain a crude product. 236.8 mg white solid T7-EA with a yield of 73.2% is obtained after a column chromatography isolation (DCM:MeOH=20:1).

Embodiment 3 for Preparation of the Compound of Formula I 516 mg (1.5 mmol) T7 and 568.3 mg (1.875 mmol) EA are dissolved in 15 mL tetrahydrofuran. HBTU (711.7 mg, 1.875 mmol), triethylamine (520 µL, 3.75 mmol) and DMAP of catalytic amount are further added and then obtained mixture is stirred at a room temperature for 18 hours for further reaction. The obtained reaction fluid is poured into 200 mL water for a suction filtration. Then the residue is washed and dried to obtain a crude product. 752 mg white solid T7-EA with a yield of 77.5% is obtained after a column chromatography isolation (DCM:MeOH=20:1).

Embodiment 4 for Preparation of the Compound of Formula I 258 mg (0.75 mmol) T7 and 265.2 mg (0.875 mmol) EA are dissolved in 10 mL N,N-dimethylacetamide. Then HBTU (332.1 mg, 0.875 mmol), triethylamine (381 µL, 2.75 mmol) and DMAP of catalytic amount are further added and then obtained mixture is stirred at a room temperature for 10 hours for further reaction. The obtained reaction fluid is poured into 100 mL water for a suction filtration. Then the residue is washed and dried to obtain a crude product. 391.6 mg white solid T7-EA with a yield of 80.7% is obtained after a column chromatography isolation (DCM:MeOH=20:1).

Embodiment 5 for Preparation of the Compound of Formula I 430 mg (1.25 mmol) T7 and 454.7 mg (1.5 mmol) EA are dissolved in 12 mL N-methylpyrrolidone. HBTU (569.3 mg, 1.5 mmol), triethylamine (485 µL, 3.5 mmol) and DMAP of catalytic amount are further added and then obtained mixture is stirred at a room temperature for 15 hours for further reaction. The obtained reaction fluid is poured into 150 mL water for a suction filtration. Then the residue is washed and dried to obtain a crude product. 645.5 mg white solid T7-EA with a yield of 79.8% is obtained after a column chromatography isolation (DCM:MeOH=20:1).

The uses for compound of formula I are studied as follows. It should be noted that in the statistical data of the following researches, the detection data are expressed in terms of Mean±SEM. Dunnet-t test and One-way ANNOVA are used for compare the difference between the treatment groups, P<0.05 represents that there is a statistically significant difference.

The used materials comprise animal and cell strain BALB/c mice, female, 5-6 weeks old, provided by the Guangdong Medical Laboratory Animal Center; and murine melanoma cell line B16f10 purchased from Shanghai ATCC Cell Bank.

The used reagents comprise RPMI-1640 culture medium and fetal bovine serum purchased from Gibco company, USA; 0.25% pancreatin purchased from Hyclone company, USA; IL-12, TNF-α, IFN-γ ELISA kits purchased from eBioscience company, USA; LDH non-radioactive cytotoxicity assays purchased from Promega company, USA; DMSO purchased from Sigma company, USA; murine lymphocyte separating medium purchased from Dakewe Biotech Co., Ltd., Beijing; PBS buffer purchased from Solarbio; CCK8 kits purchased from Dojindo Institute of Chemistry, Japan; and 75% medical ethanol purchased from Sinopharm Chemical Reagent Beijing Co., Ltd.

Figure 3A:
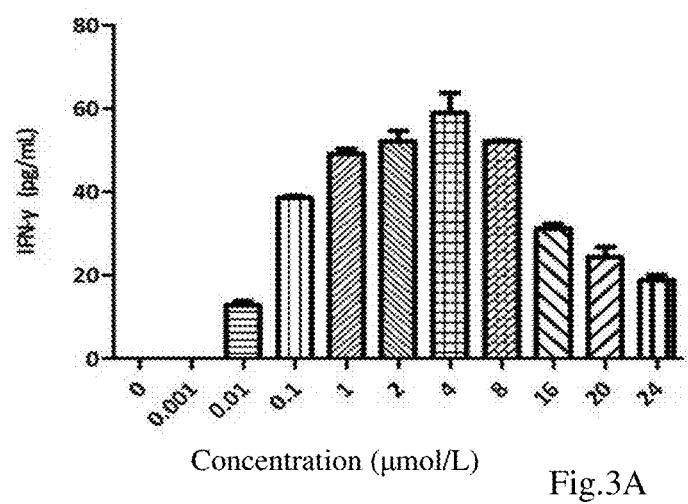
FIG. 3A is a comparative diagram showing the induction effects of the compound of formula I T7-EA of different concentrations on the generation of IFN-γ by splenic lymphocytes in vitro.
Figure 3B:
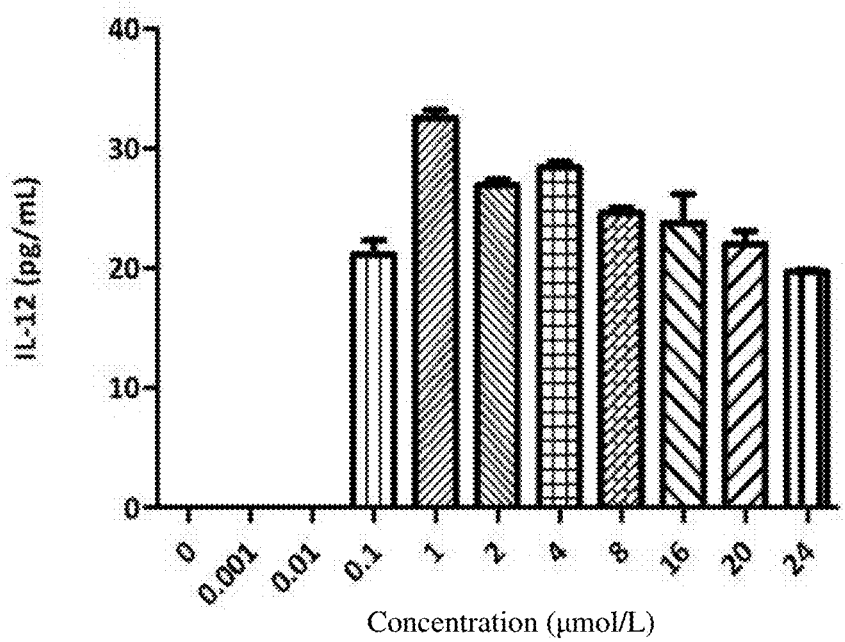
FIG. 3B is a comparative diagram showing the induction effects of the compound of formula I T7-EA of different concentrations on the generation of IL-12 by splenic lymphocytes in vitro.

Embodiment 1 for Research of the Compound of Formula I: ELISA Detection of IFN-γ and IL-12 after Stimulation of Spleen Lymphocytes In Vitro by T7-EA The mice are broken the neck to death and soaked in 75% ethanol for 5 minutes, and then placed on the super-clean bench for taking the spleen out with a sterile operation. The spleen is grinded in the 35 mm culture dish containing 4-5 ml murine lymphocyte separating medium. Then obtained cell suspension is transferred to the 15 ml centrifuge tube in which 500 μl RPMI-1640 is gently added along the tube wall for enclosure. After that the centrifuge tube is centrifuged for 30 minutes at 800 G. Then the centrifuged layer containing the lymphocytes is further centrifuged at 250 G for 10 minutes in a centrifuge tube containing 10 ml culture medium. The supernatant is discarded and the cell pellet is dissipated by the culture medium and counted. The spleen leukomonocytes are deposited on the 24-well plate with a cell density of $1 \times 10^6$/ml. T7-EA with corresponding concentrations (0, 0.001, 0.01, 0.1, 1, 2, 4, 8, 16, 20, 24 μmol/L) is added into each well and incubated for 24 hours in the cell culture box of 5% $CO_2$ and saturated humidity at 37° C. The supernatant is collected on the second day and tested according to the operation manual of the ELISA kit. The supernatants are collected after stimulating the spleen lymphocytes with T7-EA of different concentrations for 24 hours, and the ELISA test results are shown in FIGS. 3A-3B. It can be seen from the FIGS. 3A-3B that the T7-EA with a lower concentration (≤4 μmol/L) has a stronger ability for activating lymphocytes, while the T7-EA with a higher concentration (>4 μmol/L) has a decreased ability for activating lymphocytes.

Figure 4:
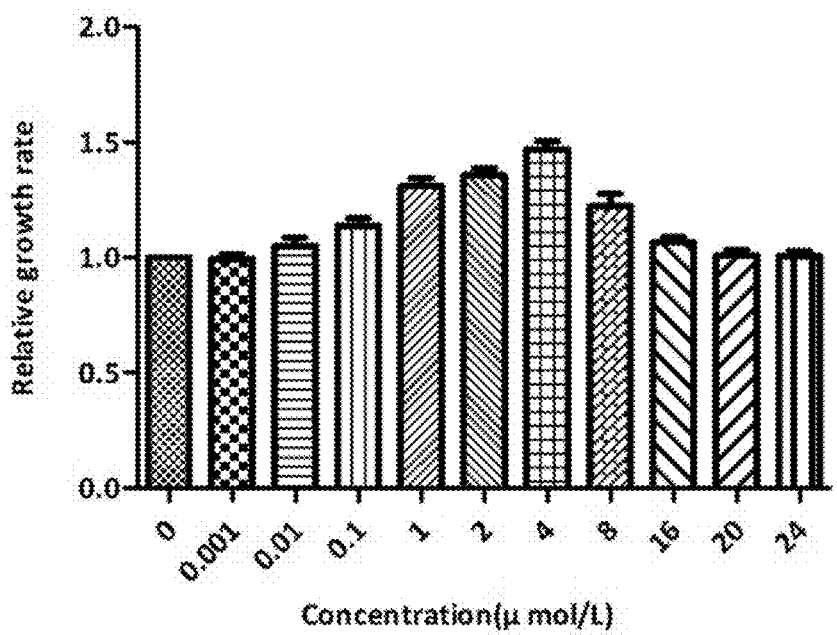
FIG. 4 is a comparative diagram showing the effects of the compound of formula I T7-EA of different concentrations on the proliferation of cytotoxic T lymphocytes.

Embodiment 2 for Research of the Compound of Formula I: Lymphocyte Proliferation Experiment The activation and proliferation abilities of T7-EA on the lymphocytes are detected. The mice are broken the neck to death and soaked in 75% ethanol, and then placed on the super-clean bench for taking the spleen out with a sterile operation. The spleen is grinded in the 35 mm culture dish containing 4-5 ml murine lymphocyte separating medium. Then obtained cell suspension is transferred to the 15 ml centrifuge tube in which 500 μl RPMI-1640 is gently added along the tube wall for enclosure. After that the centrifuge tube is centrifuged for 30 minutes at 800 G. Then the centrifuged layer containing the lymphocytes is further centrifuged at 250 G for 10 minutes in a centrifuge tube containing 10 ml culture medium. The supernatant is discarded and the cell pellet is dissipated by the culture medium and counted. The spleen leukomonocytes are deposited on the 96-well plate with a cell density of $2 \times 10^5$/each well. T7-EA with corresponding concentrations (0, 0.001, 0.01, 0.1, 1, 2, 4, 8, 16, 20, 24 μmol/L) is added onto the 96-well plate and incubated for 24 hours in the cell culture box of 5% $CO_2$ and saturated humidity at 37° C. The effect of the T7-EA on the proliferation of the lymphocytes is detected by CCK8 after the 24 hours incubation according to the operation manual of the CCK8 kits, and the results are shown in FIG. 4. It can be seen from the FIG. 4 that the T7-EA with a lower concentration (≤4 μmol/L) can promote the proliferation of the lymphocytes while the T7-EA with a higher concentration (>4 μmol/L) has no effect on the proliferation of the lymphocytes and no lethal effect on the lymphocytes. When the T7-EA has a concentration of 4 μmol/L, the relative proliferation rate is about 50%.

Figure 5:
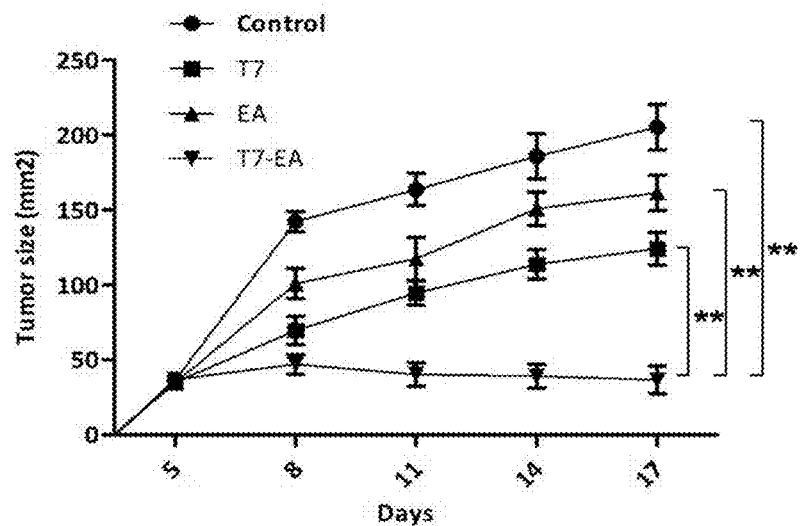
FIG. 5 is a comparative diagram showing the effects of the compound of formula I T7-EA group, T7 group, EA group and the control group on the growth of the tumor cells.

Embodiment 3 for Research of the Compound of Formula I: Anti Tumor Experiment of T7-EA In Vivo 24 4-5 weeks old female BALB/c mice are loaded with $5 \times 10^5$ tumor cells/each one after 1 weeks of quarantine at SPF level in an animal room. The mice bearing tumors are randomly divided into 75% ethanol control group, T7 group, EA group and T7-EA group, when the diameter of the tumor reaches 5 mm. The corresponding drugs are given to each group with a dosage of T7-EA 10 mg/Kg, T7 5 mg/kg, EA 12.5 mg/kg once every three days for 2 weeks. During the treatment, the tumor growth is observed by measuring the tumor size every three days. The tumor surface area is calculated according to the following formula: S=tab (wherein a represents the long diameter, while b represents the short diameter). The 24 mice are loaded with $5 \times 10^5$ tumor cells/each one after 7 days of quarantine at SPF level in an animal room. The mice bearing tumors are randomly divided into 75% ethanol control group, T7 group, EA group and T7-EA group, when the diameter of the tumor reaches 5 mm. The corresponding drugs are given to each group once every three days for 2 weeks, and the tumor size is measured every three days. The obtained tumor surface area is shown in FIG. 5, from which it is noted that the T7-EA group has significantly inhibited the growth of the tumor when comparing with the control group, T7 group and EA group and such results have a statistic difference (P<0.01).

Embodiment 4 for Research of the Compound of Formula I: CTL Experiment

Figure 6:
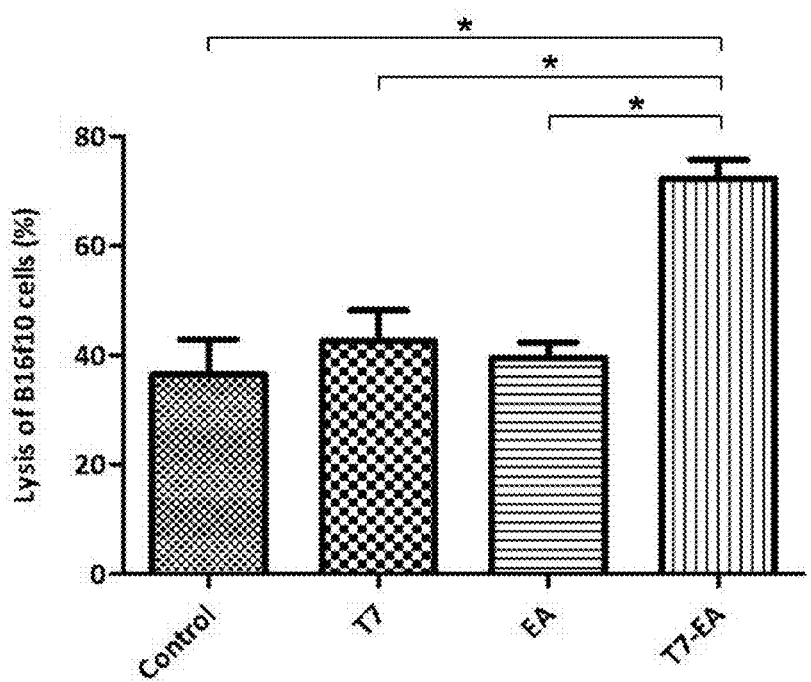
FIG. 6 is a comparative diagram showing the reaction of the cytotoxic T lymphocytes caused by the compound of formula I T7-EA group, T7 group, EA group and the control group.

The activity of cytotoxic T lymphocyte (CTL) is determined by the method of Lactic dehydrogenase (LDH) with CytoTox96Promega kits. The mice in the experimental group are broken the neck to death. The spleen lymphocytes are taken as the effector cells while the B16f10 melanoma cells are used as the target cells. The effector cells and the target cells are mixed up with a ratio of 50:1 and cultured for 4 hours. The specific operation steps can be implemented according to the operation manual, while the kill rate can calculated as follows: the killing rate (%)=(OD value of the experimental group−pontaneous OD value of the effector cells−pontaneous OD value of the target cells)/(Maximum OD value of the target cells−pontaneous OD value of the target cells)×100%. The mice in the experimental group are broken the neck to death after two weeks of administration. The spleen lymphocytes are taken as the effector cells while the B16f10 melanoma cells are used as the target cells. The effector cells and the target cells are spread onto 96-well U-shape plate according to a ratio of 50:1 and cultured together for 4 hours. The experiment results, as shown in FIG. 6, show that the T7-EA group is significantly different from the PBS group (P<0.05), while the T7-EA group is also significantly different from the T7 group and EA group (P<0.05), which indicate that T7-EA group has a stronger immune killing effect on melanoma when comparing with the control group, T7 group and EA group.

The in vivo experimental data of the above researches show that the coupling compound of T7 and EA, that is T7-EA, has a better treatment effect on melanoma than that of T7, or EA alone.

The new synthesized compound of formula I in the present application can stimulate the innate and cellular immunity for resisting tumor while greatly improving the antitumor effect of the EA, thus exploring the antitumor and immunity synergistic drug design, and proving the immune response mechanism of the compound of formula I against melanoma.

The present application has provided a compound of formula II (short for T7-EA-ROR1) which is synthesized by the covalent binding of the compound of formula I and a third reagent ROR1 as follows:

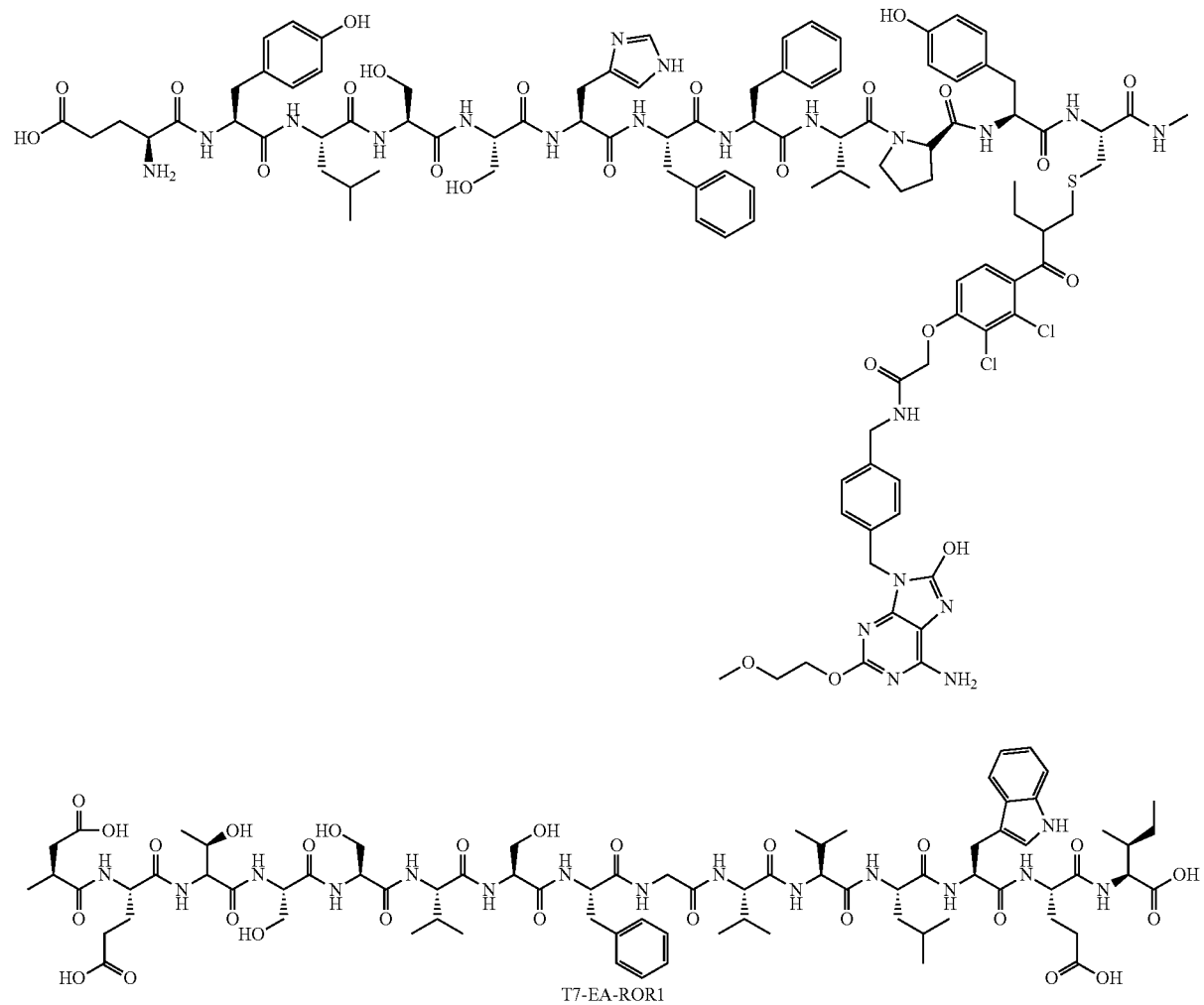

T7-EA-ROR1

Chemical Formula: $C_{177}H_{236}Cl_2N_{36}O_{50}S$
Molecular Weight: 3771.00

Wherein the third reagent is ROR1 having following formula:
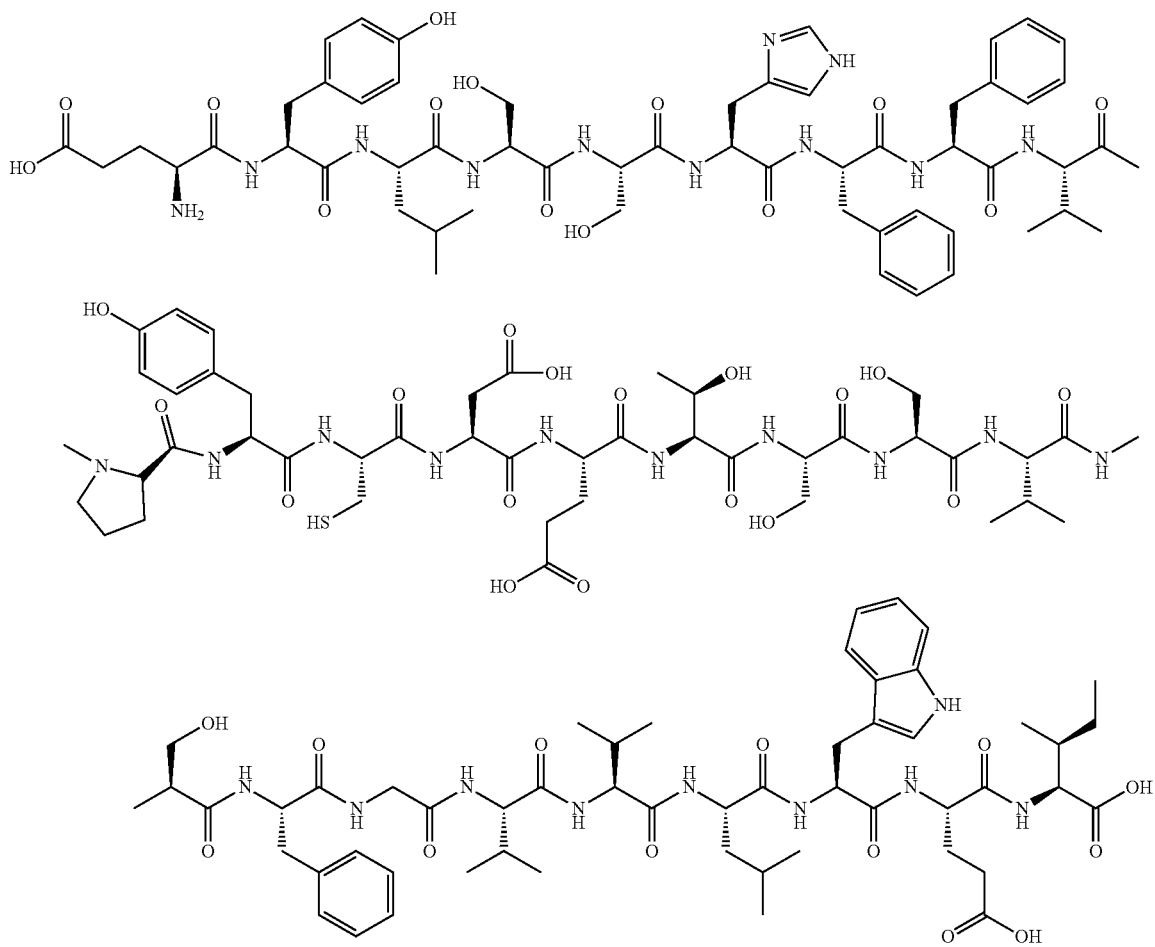
ROR1: Glu-Tyr-Leu-Ser-Ser-His-Phe-Phe-Val-Pro-Tyr-Cys-Asp-Glu-Thr-Ser-Ser-Val-Ser-Phe-Gly-Val-Val-Leu-Trp-Glu-Ile (SEQ ID NO: 1)
Chemical Formula: $C_{148}H_{206}N_{30}O_{44}S$
Molecular Weight: 3141.50
The reaction process for compound of formula II T7-EA-ROR1 is as follows:
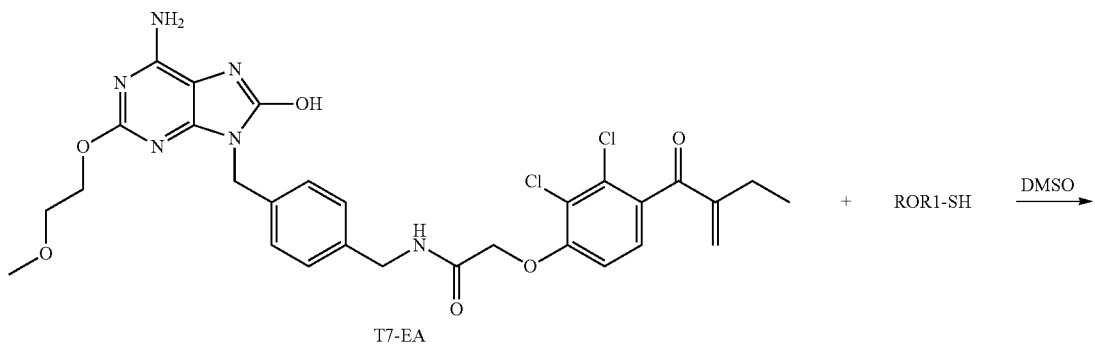
T7-EA
Chemical Formula: $C_{29}H_{30}Cl_2N_6O_6$
Molecular Weight: 629.50

-continued

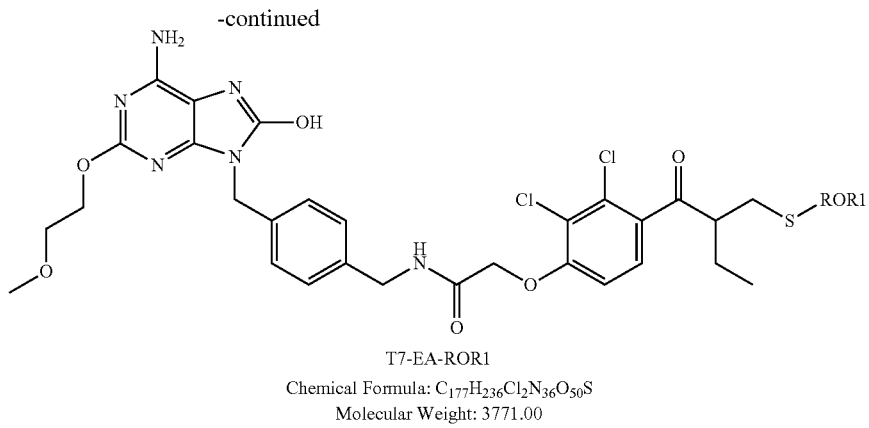

T7-EA-ROR1
Chemical Formula: $C_{177}H_{236}Cl_2N_{36}O_{50}S$
Molecular Weight: 3771.00

The specific preparation method for the compound of formula II comprises following steps. The third reagent is dissolved into dimethyl sulfoxide. Then the compound of formula I is added to stir for 8-24 hours at room temperature. The compound of formula II is obtained by using liquid chromatography-mass spectrometry to monitor reaction and prepare liquid chromatography isolation.

Figure 7:
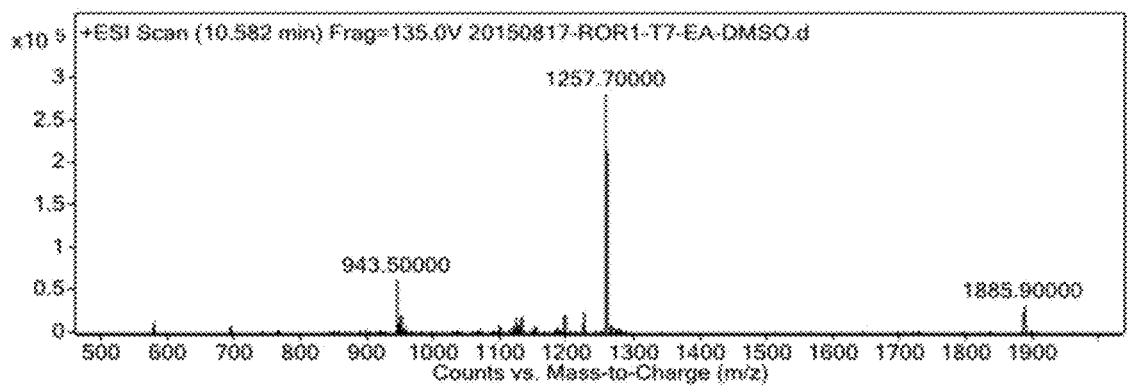
FIG. 7 is a mass spectrogram of the compound of formula II.

Embodiment 1 for Preparation of the Compound of Formula II 10 mg ROR1 is dissolved in DMSO and then T7-EA with an equimolar amount (1 eq) is added to stir at a room temperature for 12 hours. T7-EA-ROR1 with a yield of 97% is obtained by using liquid chromatography-mass spectrometry (LC-MS) to monitor reaction and prepare liquid chromatography isolation. The MS (ESI) molecular weight is in line with the theoretical value (referring FIG. 7): Measured value (1885.9×2)−1=3770.8; (1257.7×3)−2=3771.1; (943.5×4)−3=3771.0; Theoretical value 3771.0.

In other embodiments, the mixing reaction time of ROR1 and T7-EA can also be 8 hours, 15 hours or 24 hours, etc., all of these fall into the scope of protection of the present application.

The uses for the compound of formula II are studied as follows. It should be noted that in the statistical data of the following research, Graphpad Prism 6 software is used for the statistical analysis of data, and the results are expressed in terms of Mean±Standard deviation (X±S), and the pair-wise testing t-test is used for data analysis, and P<0.05 represents that there is a statistically significant difference.

The used materials comprise BALB/c mice, female, 5-6 weeks old, provided by the Guangdong Medical Laboratory Animal Center; 4T1 mammary cancer cell line purchased from Shanghai ATCC Cell Bank. The used reagents comprise ROR1 (epitopes representing ROR1 protein) synthesized by ChinaPeptides Co., Ltd., Shanghai; RPMI-1640 medium and fetal bovine serum purchased from Gibco company, USA; 0.25% pancreatin purchased from Hyclone company, USA; IL-12, TNF-α, IFN-γ ELISA kits purchased from eBioscience company, USA; CytoTox96 non-radioactive cytotoxicity assays purchased from Promega company, USA; BCA protein quantitative Kits purchased from Nan-Jing KeyGen Biotech Co., Ltd; DMSO purchased from Sigma company, USA; murine lymphocyte separating medium purchased from Dakewe Biotech Co., Ltd., Beijing; PBS buffer purchased from Solarbio company; whole-cell protein lysate purchased from Beyotime Biotechnology Co., Ltd.; rabbit anti-mouse antibody purchased from Cell signaling technology; X-VIVO purchased from Lonza; cytokine: GM-CSF, IL-4 purchased from PeproTech company; T7-EA synthesized and provided by the Shenzhen synthetic biology engineering laboratory of Shenzhen University.

Embodiment 1 for Research of the Compound of Formula II: Prediction and Synthesis of Cytotoxic T Lymphocyte (CTL) Epitope of Mammary Cancer Associated Antigen ROR1

The National Center for Biotechnology Information (NCBI) is used for searching for the full-length sequence of amino acids (M937) of ROR1, The CD8+T cell epitope is predicted by using the MHC prediction software (the URL: http://www.syfpeithi.de/bin/MHC_Server.dll/EpitopePrediction.htm) provided by the Biology Center of University Heidelberg, and six peptide epitope sequences with high scores are listed, wherein one of which is used as the epitope peptide for research. The ROR1 polypeptide is synthesized by ChinaPeptides Co., Ltd., Shanghai.

The prediction results of the ROR1 CTL epitope is shown in table 1, from which one sequence having the high scores and containing the sulfhydryl group (that is, PYCDETSSV (SEQ ID NO: 2)) is selected as the epitope peptide of this experiment. This sequence is synthesized by ChinaPeptides Co., Ltd., Shanghai and has a peptide purity over 95%.

TABLE 1

CTL epitope sequences of ROR1 predicted by syfpeithi

| Peptide (origin) | Amino acids position | Sequence | Score |
|---|---|---|---|
| ROR1$_{233}$ | 233-241 | PYCDETSSV (SEQ ID NO: 2) | 22 |
| ROR1$_{604}$ | 604-612 | EYLSSHFFV (SEQ ID NO: 3) | 25 |
| ROR1$_{677}$ | 677-685 | SFGVVLWEI (SEQ ID NO: 4) | 23 |
| ROR1$_{492}$ | 492-500 | LYLPGMDHA (SEQ ID NO: 5) | 22 |
| ROR1$_{591}$ | 591-599 | DFLHIAIQI (SEQ ID NO: 6) | 21 |
| ROR1$_{693}$ | 693-701 | YYGFSNQEV (SEQ ID NO: 7) | 21 |

Figure 8A:
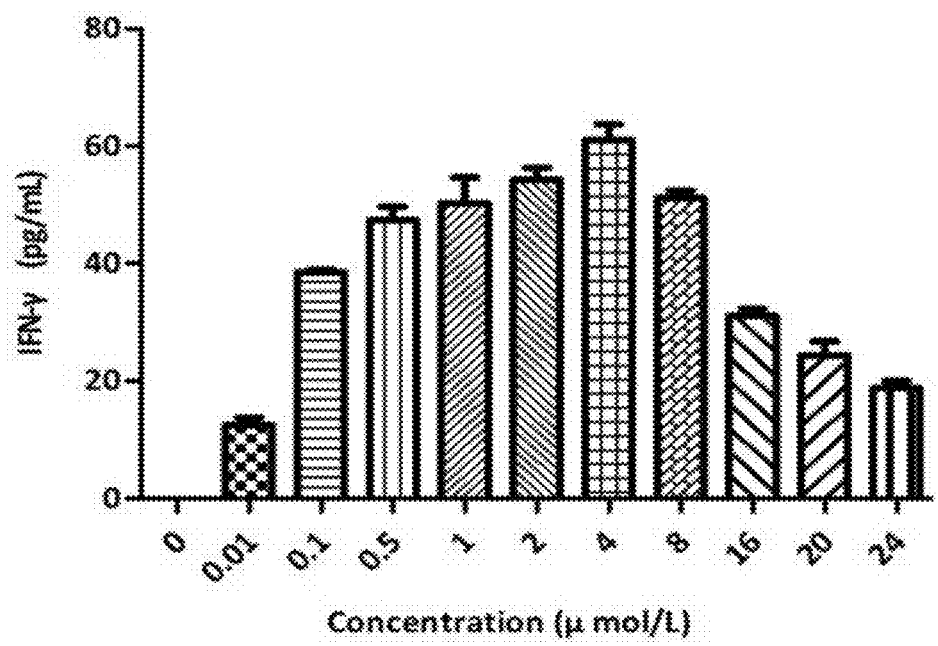
FIG. 8A is a comparative diagram showing the induction effects of the T7-EA of different concentrations on the generation of IFN-γ by splenic lymphocytes.
Figure 8B:
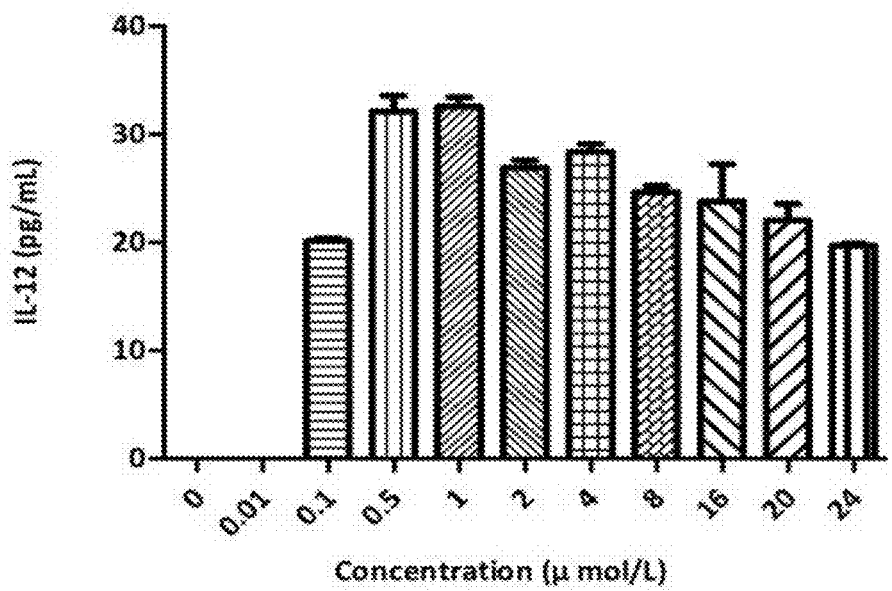
FIG. 8B is a comparative diagram showing the induction effects of T7-EA of different concentrations on the generation of IL-12 by splenic lymphocytes.

Embodiment 2 for Research of the Compound of Formula II: ELISA Detection of Cytokines IFN-γ and IL-12 Generated by Spleen Lymphocytes after Stimulation of T7-EA The mice are broken the neck to death and soaked in 75% ethanol, and then placed on the super-clean bench for taking the spleen out with a sterile operation. The spleen is grinded in the 35 mm culture dish containing 4-5 ml Mouse1× lymphocyte separating medium. Then separating medium suspended with spleen cells is transferred to the 15 ml centrifuge tube and enclosed with 500 μl RPMI-1640, After that the centrifuge tube is centrifuged at room temperature for 30 minutes at 800 G. Then the middle buffy coat is placed into a centrifuge tube containing 10 ml culture medium for being overthrown and washed. After that, the centrifuge tube is further centrifuged at 250 G for 10 minutes at room temperature. The supernatant is discarded and the cell pellet is dissipated by the culture medium and counted. The spleen leukomonocytes are deposited on the 24-well plate with a final cell density of $1\times10^6$/ml. T7-EA with corresponding concentrations (0, 0.01, 0.1, 0.5, 1, 2, 4, 8, 16, 20, 24 μmol/L) is added and incubated for 24 hours in the cell culture box. The supernatant is collected on the second day and tested according to the operation manual of the ELISA kit. As shown in FIGS. 8A-8B, the T7-EA can activate the lymphocytes and induce the lymphocytes to generate cytokines IFN-γ and IL-12. When the T7-EA has a concentration ≤4 μmol/L, better effects can be obtained. Accordingly, 4 μmol/L is the effective concentration of the T7-EA.

Embodiment 3 for Research of the Compound of Formula II: ELISA Detection of Cytokines TNF-α Generated by DC after Combined Stimulation of T7-EA and ROR1

Figure 9:
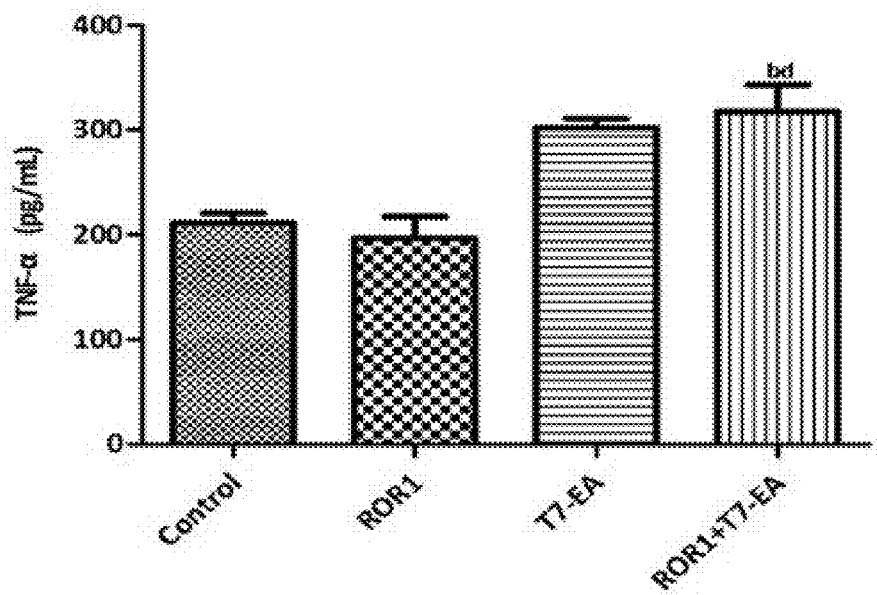
FIG. 9 is a comparative diagram showing the cytokine TNF-α generated via stimulating dendritic cells by the compound of formula II T7-EA-ROR1 group, T7-EA group, ROR1 group and the control group.

The mice are broken the neck to death and soaked in 75% ethanol, and then fixed on the stencil plate for taking the femur of the Lower extremities out with a sterile operation on the super-clean bench. The bone marrow cavity is flushed with PBS (2% FBS) via 1 mL syringe to flush out the bone marrow which is then filtered by the BD screen to collect the cells in the 15 mL centrifuge tube. Then the centrifuge tube is centrifuged to remove the supernatant (1400 rpm, 5 min, 4° C.), and then 1 mL erythrocyte lysate is added for resuspending. After 1 min of standing, 3 mL complete culture medium is added for termination. Then obtained reactant is further centrifugated (1400 rpm, 5 min, 4° C.) for removing the supernatant. 1640 complete culture medium containing $Ca^{2+}Mg^{2+}$ is used to resuspend and the obtained suspension is cultured in 100 mm culture dish for adherent growth of 6 hours. Then cell pellet is dissipated, collected and counted, and then further resuspended with X-VIVO complete culture medium (with a cytokines concentration of GM-CSF 20 ng/mL, IL-4 10 ng/mL, respectively), and then planted on 24-well plate with a final cell concentration of $1\times10^6$/mL. Then the cells are cultured in the cell culture box of 5% $CO_2$ and saturated humidity at 37° C. Half of the culture medium is replaced on the third and fifth day, and T7-EA, ROR1, T7-EA-ROR1 are added to stimulate the dendritic cells for 24 hours on the sixth day. The final T7-EA concentration is 4 μmol/L, and the T7-EA-ROR1 group has a mixing molar ratio of 1:1 for the T7-EA and ROR1. The cells harvested at the seventh day is centrifugated (1400 rpm, 5 min, 4° C.), and then the supernate is collected for TNF-α detection according to the operation manual of the ELISA kit. As shown in FIG. 9, in terms of the amount of cytokine TNF-α, there is a significant difference between the T7-EA-ROR1 group and the PBS control group (P<0.01), and there is also a significant difference between the T7-EA-ROR1 group and the ROR1 group (P<0.01).

Embodiment 4 for Research of the Compound of Formula II: ELISA Detection of Cytokines IFN-γ and IL-12 Generated by Spleen Lymphocytes after Stimulation of T7-EA-ROR1

Figure 10A:
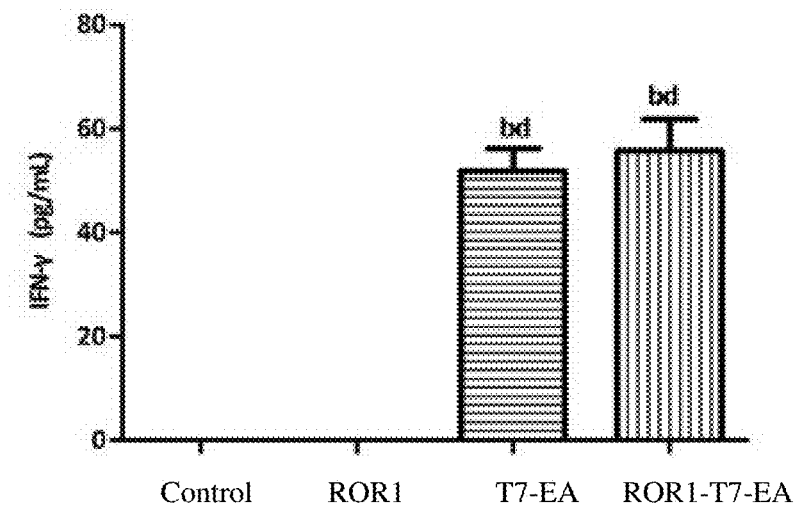
FIG. 10A is a comparative diagram showing the cytokine IFN-γ generated via stimulating dendritic cells by the compound of formula II T7-EA-ROR1 group, T7-EA group, ROR1 group and the control group.
Figure 10B:
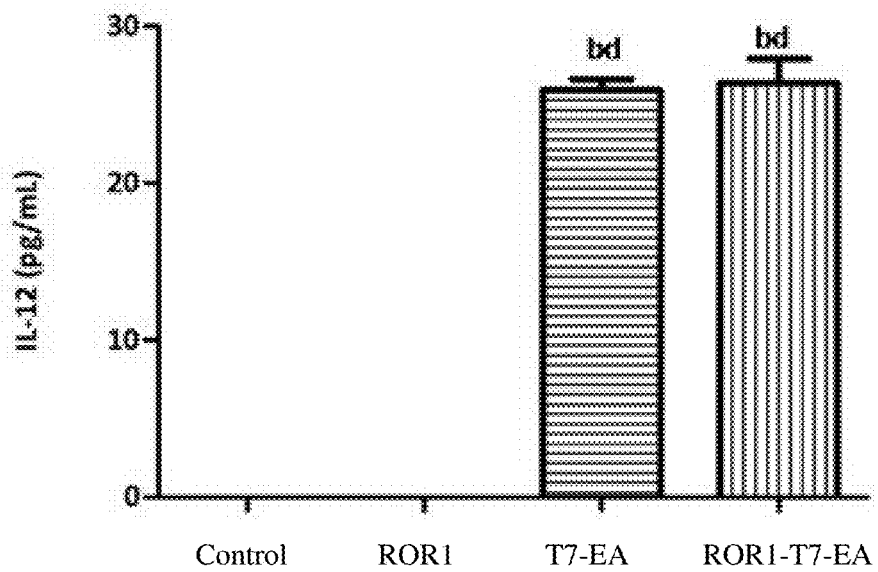
FIG. 10B is a comparative diagram showing the cytokine IL-12 generated via stimulating dendritic cells by the compound of formula II T7-EA-ROR1 group, T7-EA group, ROR1 group and the control group.

The specific operation method for the extraction of murine spleen lymphocytes is just same as that of the Embodiment 2 for research of the compound of formula II. The final T7-EA concentration is 4 μmol/L, and the T7-EA-ROR1 group has a mixing molar ratio of 1:1 for the T7-EA and ROR1. The supernate is collected at the second day for cytokines IFN-γ and IL-12 detection according to the operation manual of the ELISA kit. Results are shown in FIGS. 10A-10B, in which the PBS control group and the ROR1 group cannot induce the spleen lymphocytes to generate cytokines IFN-γ and IL-12, while the T7-EA-ROR1 group and the T7-EA group can induce the spleen lymphocytes to generate cytokines IFN-γ and IL-12. Accordingly, there is a significant difference between the T7-EA-ROR1 group and the T7-EA group, and the PBS control group and the ROR1 group (P<0.01).

Figure 11A:
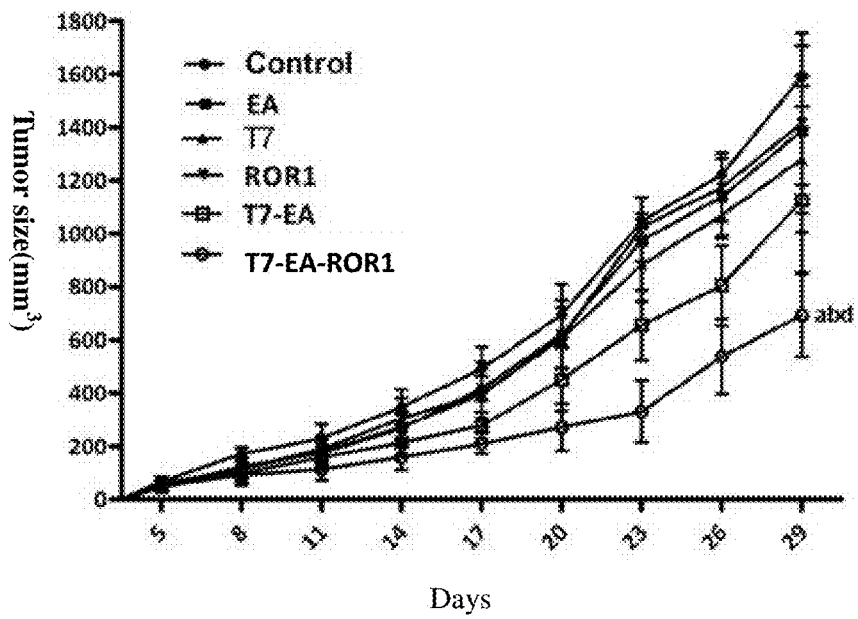
FIG. 11A is a comparative diagram showing the tumor growth trend of the compound of formula II T7-EA-ROR1 group, T7-EA group, ROR1 group and the control group.
Figure 11B:
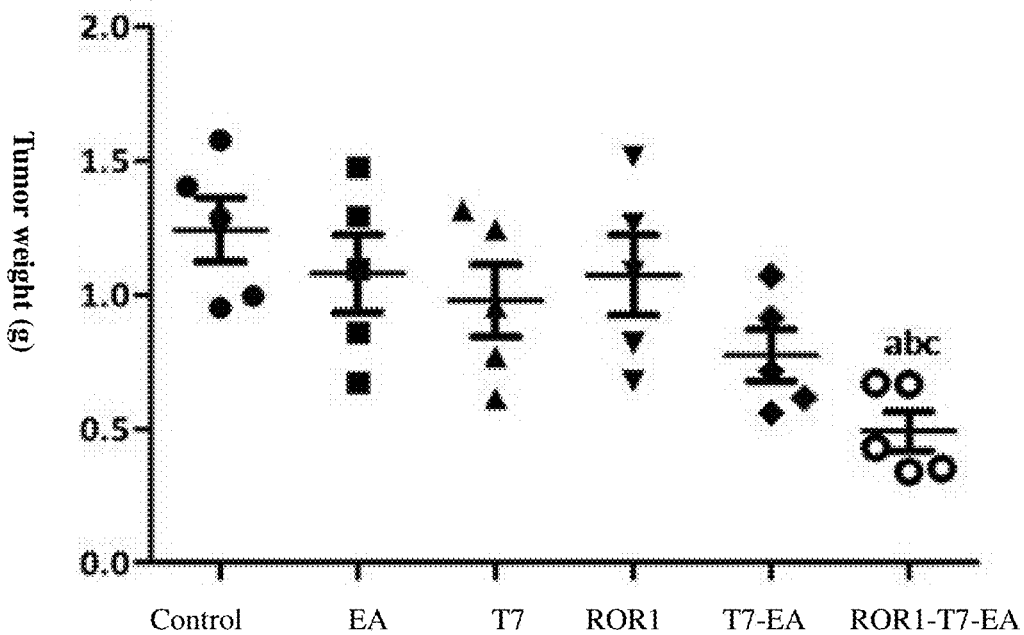
FIG. 11B is a comparative diagram showing the tumor weight of the compound of formula II T7-EA-ROR1 group, T7 group, EA group, T7-EA group, ROR1 group and the control group.
Figure 11C:
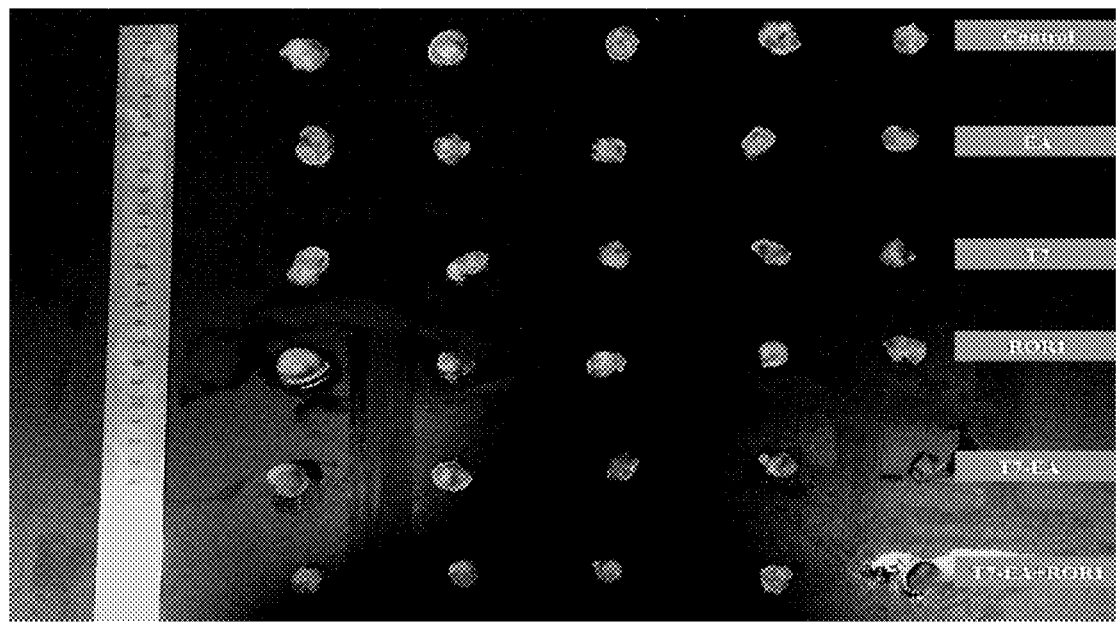
FIG. 11C is a comparative diagram showing the tumor size of the compound of formula II T7-EA-ROR1 group, T7 group, EA group, T7-EA group, ROR1 group and the control group.

Embodiment 5 for Research of the Compound of Formula II: Anti Tumor Experiment on Animals 36 4-5 weeks old female BALB/c mice are loaded with $2\times10^5$ mammary cancer 4T1 cells/each one after 1 weeks of quarantine at SPF level in an animal room. The mice bearing tumors are randomly divided into PBS control group, T7 group, EA group, T7-EA group, ROR1 group and T7-EA-ROR1 group, when the diameter of the tumor reaches 5 mm. The corresponding drugs are given to each group via intraperitoneal administration for immunotherapy once a week, and four times in total. The mice are killed for taking out their spleen and tumor on the sixth days after the last immunotherapy. The tumor size is calculated according to the following formula: $V=ab^2/2$ (wherein a represents the long diameter, while b represents the short diameter). The obtained tumor size is shown in FIG. 11A-11C, from which it is noted that the T7-EA-ROR1 group has significantly slower tumor growth speed when comparing with the PBS control group and the ROR1 group and such results have a statistic difference (P<0.01), while the T7-EA-ROR1 group further has significantly slower tumor growth speed when comparing with the T7-EA group (P<0.05). The tumor weight is in accordance with the tumor growth. The tumor weight of T7-EA-ROR1 group is lighter than that of the PBS group (P<0.01). Compared with T7-EA group, the tumor weight of T7-EA-ROR1 group decreases significantly (P<0.05), while the tumor weight of T7-EA-ROR1 group is also significantly smaller than that of ROR1 group (P<0.05).

Figure 12:
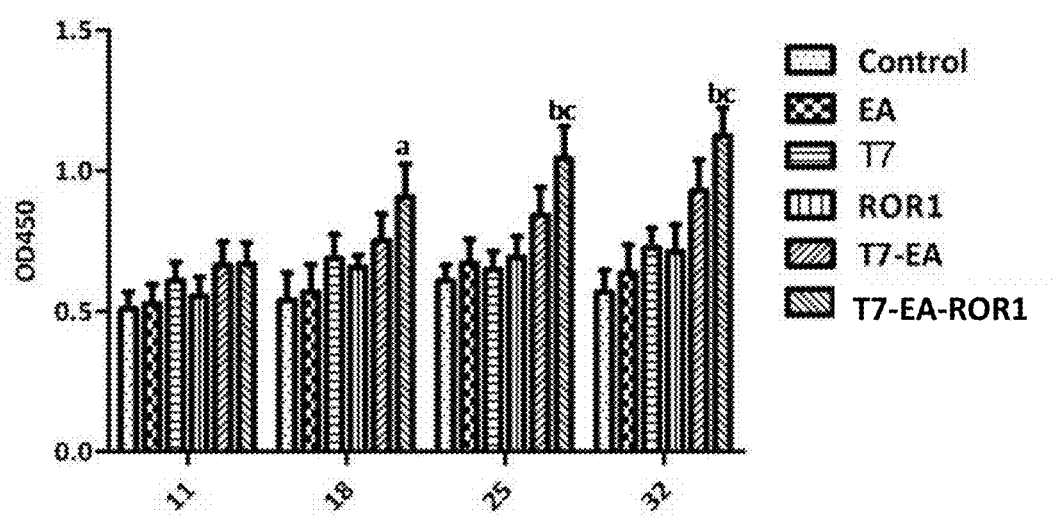
FIG. 12 is a comparative diagram showing the effects on the generation of the antibody IgG by the human body of the compound of formula II T7-EA-ROR1 group, T7 group, EA group, T7-EA group, ROR1 group and the control group.

Embodiment 6 for Research of the Compound of Formula II: Whole-Cell Antibody Detection The protein of mammary cancer 4T1 cells is extracted and the concentration of which is also measured in accordance with the operation manual of the BCA protein quantitative kits. The extracted protein is used as the envelope antigen. The venous blood of mice is collected sixth days after each immunotherapy, and its supernatant is collected for 4 times. The serum antibody is measured in accordance with the operation manual of the ELISA kit. As results shown in FIG. 12, the level of IgG antibody in the mice sera of group T7-EA and group T7-EA-ROR1 increases gradually with the increase of immunization times. In term of the amount of antibody IgG, there is a significant difference between the T7-EA-ROR1 group and the PBS group (P<0.01). The IgG antibody produced in the T7-EA-ROR1 group is also significantly different from that of the ROR1 group (P<0.05). The above results show that T7-EA has increased the immunogenicity of ROR1, and the T7-EA-ROR1 has induced the human body to generate a humoral immune response.

Embodiment 7 for Research of the Compound of Formula II: CTL Activity Detection

Figure 13:
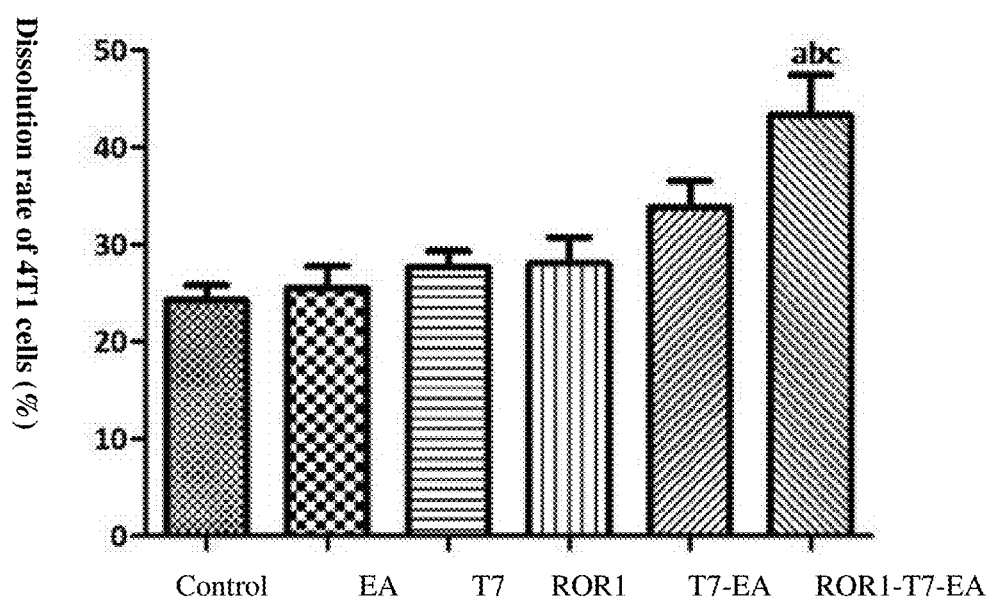
FIG. 13 is a comparative diagram showing the reaction of the cytotoxic T lymphocytes caused by the compound of formula II T7-EA-ROR1 group, T7 group, EA group, T7-EA group, ROR1 group and the control group.

The activity of cytotoxic T lymphocyte (CTL) is determined by the method of Lactic dehydrogenase (LDH) in accordance with the operation manual of the LDH kits. The specific operation method for the extraction of murine spleen lymphocytes is just same as that of the Embodiment 2 for research of the compound of formula II. The extracted spleen lymphocytes are taken as the effector cells while the mammary cancer 4T1 cells are used as the target cells. The effector cells and the target cells are mixed up with a ratio of 25:1 and cultured together for 4 hours. The kill rate can calculated as follows: the killing rate (%)=(OD value of the experimental group−pontaneous OD value of the effector cells−pontaneous OD value of the target cells)/(Maximum OD value of the target cells−pontaneous OD value of the target cells)×100%. The experiment results, as shown in FIG. 13, show that the T7-EA-ROR1 group has a significantly immune killing effect on the killing function of the mammary cancer 4T1 cells when comparing with the control group (P<0.01), and a obviously stronger immune killing effect on the killing function of the mammary cancer 4T1 cells when comparing with the T7-EA group and ROR1 group (P<0.05), which indicates that the combination of T7-EA and ROR1 can better stimulate cellular immunity and enhance the lethality of vaccine against target cells.

T7-EA can stimulate splenic lymphocytes to produce cytokines IFN- and IL-12 (referring FIGS. 8A and 8B), which data indicate that T7-EA has the function of stimulating innate immunity. The results of the experiment (FIGS. 9, 10A and 10B) show that the weak immunogenicity of ROR1 cannot stimulate the innate immunity. However, the combination of T7-EA and ROR1 make the vaccine better stimulate the innate immunity. The growth of tumors (FIGS. 11A, 11C) and tumor weight (FIG. 11B) show that the combination of T7-EA and ROR1 significantly slows the tumor growth.

TLR7 is expressed in immune cells, such as macrophages, dendritic cells and B lymphocytes. After the combination of TLR7 and its agonists, the TLR7 dependent MyD88 signaling pathway is activated to produce cytokines, induce and activate dendritic cells, thus better activating B cells and T auxiliary cells and stimulating the immune effect of the body. The CTL results in this experiment (FIG. 13) show that when T7-EA is combined with ROR1, it can stimulate the activation of T cells while stimulating the innate immunity, thus better killing the target cells. The whole-cell antibody titer results (FIG. 12) indicate that the T7-EA-ROR1 induces the human body to produce specific IgG antibody against mammary cancer. These data indicate that the combination of T7-EA and ROR1 can make the vaccine better stimulate cellular immunity and humoral immunity.

To sum up, the compound of formula II T7-EA-ROR1 has significantly slowed down the growth of the subcutaneous transplantation tumor of the mammary cancer, which proves the immune response mechanism of the compound of formula II against the mammary cancer while proving that the compound of formula II not only just have the function of stimulating the innate and adaptive immunity, but also have an immunologic adjuvant effect.

It should be understood that, for one skilled in the art, the above embodiments can be improved or modified according to the above description, and all of those improvements or modifications fall into the protection scope of the attached claims of the present application.

What is claimed is:

1. A compound of formula I:

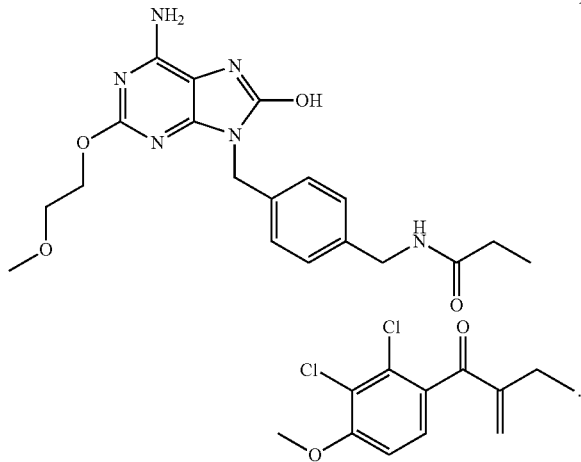

2. A preparation method for the compound of formula I according to claim 1, comprising:
step S1, dissolving a first reactant

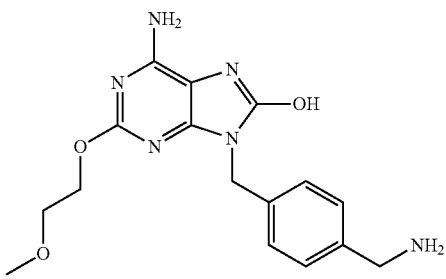 [SMILES: COCCOc1nc(N)c2nc(O)n(Cc3ccc(CN)cc3)c2n1]

and a second reactant EA

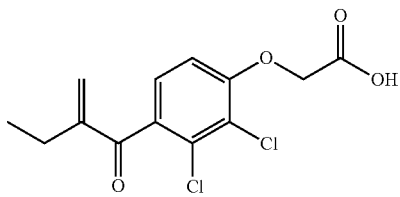 [SMILES: C=C(CC)C(=O)c1ccc(OCC(=O)O)c(Cl)c1Cl]

in a reaction solvent, then adding O-Benzotriazole-N,N,N,N-tetramethyl-uronium-hexafluorophosphate (HBTU), triethylamine, and 4-Dimethylaminopyridine wherein 4-Dimethylaminopyridine is a catalyst, and stirring obtained mixture at room temperature for reaction;

step S2, pouring reaction solution into water for a suction filtration wherein the reaction solution is obtained from step S1 after the reaction in step S1 is completed, then washing and drying residue of suction filtration to obtain the compound of formula I.

3. The preparation method for the compound of formula I according to claim 2, wherein in the step S1, the first reactant, the second first reactant, the HBTU and the triethylamine are reacted in following parts by mol: the first reagent 4-12 parts, the second first reactant 5-15 parts, the HBTU 5-15 parts and the triethylamine 18-30 parts.

4. The preparation method for the compound of formula I according to claim 2, wherein in the step S1, the first reactant, the second first reactant, the HBTU and the triethylamine are reacted in following parts by mol: the first reactant 6-10 parts, the second first reactant 7-12 parts, the HBTU 7-12 parts and the triethylamine 22-28 parts.

5. The preparation method for the compound of formula I according to claim 2, wherein in the step S1, the first reactant and the second first reactant have a mole ratio of 1:1.

6. The preparation method for the compound of formula I according to claim 2, wherein in the step S1, the reaction solvent is N,N-Dimethylformamide.

7. The preparation method for the compound of formula I according to claim 2, wherein the step S1 has a reaction time of 8-24 hours.

8. The preparation method for the compound of formula I according to claim 2, wherein the step S1 has a reaction time of 10-15 hours.

9. The preparation method for the compound of formula I according to claim 2, wherein further comprising step S3 which follows step S2: purifying obtained compound of formula I via column chromatography isolation using a mixed solvent of dichloromethane and methanol in a volume ratio of 20:1.

* * * * *